(12) United States Patent
Nishiuchi

(10) Patent No.: US 8,168,819 B2
(45) Date of Patent: May 1, 2012

(54) PROCESS FOR PRODUCTION OF 5-PHENYLISOPHTHALIC ACID

(75) Inventor: Junya Nishiuchi, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 338 days.

(21) Appl. No.: 12/295,761

(22) PCT Filed: Apr. 4, 2007

(86) PCT No.: PCT/JP2007/057548
§ 371 (c)(1),
(2), (4) Date: Oct. 2, 2008

(87) PCT Pub. No.: WO2007/116906
PCT Pub. Date: Oct. 18, 2007

(65) Prior Publication Data
US 2009/0156858 A1    Jun. 18, 2009

(30) Foreign Application Priority Data

Apr. 4, 2006    (JP) .................................. 2006-103050

(51) Int. Cl.
*C07C 51/255* (2006.01)
(52) U.S. Cl. ........ 562/412; 562/405; 562/407; 562/408; 562/409; 562/417
(58) Field of Classification Search .................... None
See application file for complete search history.

(56) References Cited

U.S. PATENT DOCUMENTS

| 5,254,768 A | 10/1993 | Kihara |
| 5,334,754 A * | 8/1994 | Sumner et al. ................ 562/416 |

FOREIGN PATENT DOCUMENTS

| JP | 62-129229 | 6/1987 |
| JP | 04-103542 | 4/1992 |
| JP | 04-275241 | 9/1992 |
| JP | 05-294891 | 11/1993 |
| JP | 05294891 A * | 11/1993 |
| JP | 08-020548 | 1/1996 |
| JP | 08020548 A * | 1/1996 |
| JP | 09-104679 | 4/1997 |
| JP | 09104679 A * | 4/1997 |

OTHER PUBLICATIONS

R. Akiyama, et al., "Microencapsulated Palladium Catalysts: Allylic Substitution and Suzuki Coupling Using a Recoverable and Reusable Polymer-Supported Palladium Catalyst", *Angew. Chem. Int. Ed.*, vol. 40, No. 18, pp. 3469-3471, 2001.
Extended European Search Report dated Sep. 15, 2010, including Supplementary European Search Report and extended European Search Opinion.
A. Singh, et al., "Gas separation properties of pendent phenyl substituted aromatic polyamides containing sulfone and hexafluoroisopropylidene groups", *Polymer*, 40 (1999), pp. 5715-5722.
P. K. Singh, et al., "Analytical Application of 200 MHz PMR Spectroscopy-Isomer Analysis in Tolylcycloalkanes", *Indian Journal of Chemistry*, vol. 24B, Jun. 1, 1985, pp. 651-653.

* cited by examiner

*Primary Examiner* — Sudhakar Katakam
(74) *Attorney, Agent, or Firm* — Antonelli, Terry, Stout & Kraus, LLP.

(57) ABSTRACT

The present invention provides an industrially advantageous process for producing 5-phenylisophthalic acid, which process attains excellent selectivity and yield and also realizes recovery and reuse of a catalyst.
The process for producing 5-phenylisophthalic acid represented by formula (1) is characterized in that the process includes the following steps (A) to (C):
(A) reacting m-xylene with cyclohexene in the presence of hydrogen fluoride and boron trifluoride, to thereby produce 1-cyclohexyl-3,5-dimethylbenzene;
(B) dehydrogenating the 1-cyclohexyl-3,5-dimethylbenzene produced in step (A) in the presence of a dehydrogenation catalyst, to thereby produce 3,5-dimethylbiphenyl; and
(C) dissolving the 3,5-dimethylbiphenyl produced in step (B) in a solvent and oxidizing the 3,5-dimethylbiphenyl in the co-presence of an oxidation catalyst, to thereby produce 5-phenylisophthalic acid.

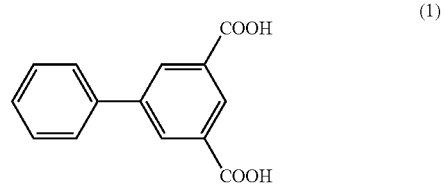

(1)

7 Claims, No Drawings

PROCESS FOR PRODUCTION OF 5-PHENYLISOPHTHALIC ACID

The present invention relates to a process for producing 5-phenylisophthalic acid, which serves as a useful starting material for producing industrial chemicals, pharmaceuticals, pesticides, optical functional materials, and electronic functional materials.

BACKGROUND ART

Hitherto, 5-phenylisophthalic acid is known to be synthesized through a process employing 1-cyclohexyl-3,5-dimethylbenzene as a starting material and a combination of hydrochloric acid and aluminum chloride serving as a catalyst. However, when this process is employed, selectivity and yield are insufficient, and the used catalyst cannot be recovered. Thus, there is demand for a process which is industrially more advantageous (see Non-Patent Document 1).

Several processes for solving the above problem have already been disclosed. In one process, 3,5-dimethylbiphenyl is synthesized through Suzuki's coupling reaction between bromobenzene and 3,5-dimethylphenylboronic acid in the presence of a transition metal compound such as tetrakis(triphenylphosphine)palladium(0), and the thus-produced 3,5-dimethylbiphenyl is oxidized with an oxidizing agent such as potassium permanganate or potassium chromate, to thereby yield 5-phenylisophthalic acid (see Non-Patent Document 2). In another process, a Grignard reagent produced from 5-bromo-m-xylene and magnesium is reacted with bromobenzene in the presence of a triphenylphosphine-nickel chloride catalyst, to thereby produce 3,5-dimethylbiphenyl, and the produced 3,5-dimethylbiphenyl is oxidized with an oxidizing agent, to thereby yield 5-phenylisophthalic acid (see Patent Document 1). Although the disclosed processes are satisfactory to some extent in terms of selectivity and yield, the processes have problems. In the process employing Suzuki's coupling reaction, an expensive transition metal complex must be used, whereas in the process employing a Grignard reagent, a step for producing the Grignard reagent considerably impairs production efficiency. Both cases are problematic. Therefore, these processes are difficult to employ as industrial production processes.

Non-Patent Document 1:
Bodroux, Coreaf, C. R. Hebd. Seances Acad. Sci., 186, 1928,
Non-Patent Document 2:
Akiyama Ryo and Kobayashi Shue, Angew. Chem. Int. Ed., EN, 40, 18, 2001, 3469-3471
Patent Document 1: Japanese Patent Application Laid-Open (kokai) No. 9-104679

DISCLOSURE OF THE INVENTION

Problems to be Solved by the Invention

Under such circumstances, an object of the present invention is to provide an industrially advantageous process for producing 5-phenylisophthalic acid, which process attains excellent selectivity and yield and realizes recovery and reuse of a catalyst.

Means for Solving the Problems

The present inventors have carried out extensive studies on an industrially advantageous process for producing 5-phenylisophthalic acid and have found that 5-phenylisophthalic acid can be selectively produced through alkylating m-xylene with cyclohexene, to thereby selectively produce 1-cyclohexyl-3,5-dimethylbenzene, dehydrogenating the product to form a biphenyl skeleton, and oxidizing the biphenyl species. The present invention has been accomplished on the basis of this finding.

Accordingly, the present invention provides the following.
(1) A process for producing 5-phenylisophthalic acid represented by formula (I):

[F1]

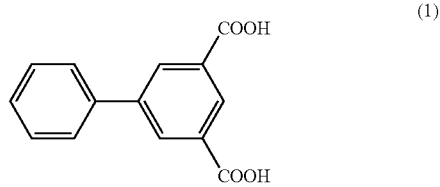

characterized in that the process comprises the following steps (A) to (C):
(A) reacting m-xylene with cyclohexene in the presence of hydrogen fluoride and boron trifluoride, to thereby produce 1-cyclohexyl-3,5-dimethylbenzene;
(B) dehydrogenating the 1-cyclohexyl-3,5-dimethylbenzene produced in step (A) in the presence of a dehydrogenation catalyst, to thereby produce 3,5-dimethylbiphenyl; and
(C) dissolving the 3,5-dimethylbiphenyl produced in step (B) in a solvent and oxidizing the 3,5-dimethylbiphenyl in the co-presence of an oxidation catalyst, to thereby produce 5-phenylisophthalic acid.
(2) A process for producing 5-phenylisophthalic acid as described in (1) above, wherein, in step (A), m-xylene is alkylated with cyclohexene in the presence of hydrogen fluoride and, subsequently, isomerization/transalkylation is performed in the presence of hydrogen fluoride and boron trifluoride.
(3) A process for producing 5-phenylisophthalic acid as described in (1) or (2) above, wherein, in step (A), hydrogen fluoride and boron trifluoride are recovered and reused.
(4) A process for producing 5-phenylisophthalic acid as described in (1), wherein the dehydrogenation catalyst employed in step (B) is a catalyst containing platinum and/or palladium, supported on a carrier.
(5) A process for producing 5-phenylisophthalic acid as described in (1), wherein, in step (C), the solvent is an aliphatic monocarboxylic acid solvent; the oxidation catalyst is a catalyst containing a cobalt atom, a manganese atom, and a bromine atom; and oxidation is performed by an oxygen-containing gas.
(6) A process for producing 5-phenylisophthalic acid as described in (5), wherein the solvent is acetic acid, and the oxidation catalyst contains cobalt acetate, manganese acetate, and hydrogen bromide.

Effects of the Invention

According to the process of the present invention, 5-phenylisophthalic acid can be produced at high selectivity and high yield and in an industrially advantageous manner which realizes recovery and reuse of the catalysts.

BEST MODES FOR CARRYING OUT THE INVENTION

<Step (A)>

In step (A), represented by the following reaction scheme (2):

[F2]

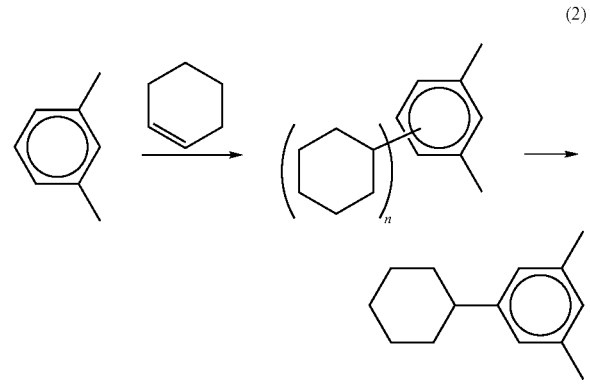

(2)

(wherein n is an integer of 0 to 4), 1-cyclohexyl-3,5-dimethylbenzene is produced by reacting m-xylene with cyclohexene in the presence of hydrogen fluoride and boron trifluoride.

A characteristic feature of step (A) resides in use of hydrogen fluoride (hereinafter referred to as HF) and boron trifluoride (hereinafter referred to as $BF_3$) in combination as a catalyst. Through use of these catalysts in combination, considerably high selectivity and high yield of the target product can be attained, and the catalysts can be recovered and reused, making step (A) industrially advantageous.

When the reaction between m-xylene and cyclohexene is carried out in the presence of HF and $BF_3$, 1-cyclohexyl-3,5-dimethylbenzene can be formed via a single-step alkylation/isomerization. Since the single-step reaction reduces the number of operation steps, the step is industrially advantageous. Alternatively, the reaction between m-xylene and cyclohexene may also be carried out as a two-step reaction including alkylation in which polycyclohexyl-m-xylene is synthesized from m-xylene in the presence of HF, and transalkylation/isomerization in which 1-cyclohexyl-3,5-dimethylbenzene is synthesized from the formed polycyclohexyl-m-xylene in the presence of HF and $BF_3$. When the reaction between m-xylene and cyclohexene is performed in a two-step manner, polycyclohexyl-m-xylene species (n≧2) do not remain in a large amount; i.e., the amount of remaining polycyclohexyl-m-xylene is reduced, which is preferred from the viewpoint of yield.

<Step (A): Single-Step Reaction>

In the single-step reaction, no particular limitation is imposed on the reaction format, so long as the format ensures sufficient mixing of liquid phases through stirring. For example, any of batch, semi-batch, continuous, and other suitable reaction formats may be employed. Of these, semi-batch and continuous formats are preferably employed from the viewpoint of yield. In one specific embodiment of a semi-batch format, a liquid mixture of cyclohexene and m-xylene is fed to a reactor in which HF and $BF_3$ have been placed, and the reaction mixture is poured in ice-water, whereby 1-cyclohexyl-3,5-dimethylbenzene is recovered. In another embodiment of a continuous format, HF, $BF_3$, m-xylene, and cyclohexene are fed to a reaction tank, and the reaction mixture is transferred from the bottom of the reaction tank to ice or is decomposed by heat. Through continuously performing these operations, 1-cyclohexyl-3,5-dimethylbenzene can be produced.

In the single-step reaction, the ratio by mole of cyclohexene to m-xylene employed in alkylation/isomerization of step (A), represented by cyclohexene/m-xylene, is 0.5 to 2.0 (mole), preferably 1.0 to 1.3 (mole). Such a limitation in range of amount of cyclohexene is also preferred from the viewpoint of production efficiency, since polycycloheyl-m-xylene can be efficiently produced.

In the single-step reaction, HF employed in alkylation/isomerization of step (A) is preferably a virtually anhydrous species, from the viewpoint of corrosion prevention of a reactor and other equipment. The ratio by mole HF to m-xylene, represented by HF/m-xylene, is 2 to 10 (mole), preferably 3 to 8 (mole). Such a limitation in range of amount of HF is advantageous from the viewpoint of production efficiency, since alkylation can be proceeded efficiently, and a large-scale reactor and a large-scale HF recovery unit are not needed. The ratio by mole of $BF_3$ to m-xylene, represented by $BF_3$/m-xylene, is 1.1 to 3.0 (mole), preferably 1.5 to 2.0 (mole). Such a limitation in range of amount of $BF_3$ is preferred, since a favorable isomerization rate is maintained, and high production efficiency can be attained.

In the single-step reaction, alkylation/isomerization of step (A) is preferably performed at −20° C. to 20° C., more preferably −10° C. to 10° C., which is recommended from the viewpoint of attaining the maximum reactivity. Such a limitation in range of reaction temperature is preferred, since side reactions such as rearrangement of a methyl group and isomerization from a cyclohexyl group to a methylcyclopentyl compound are considerably suppressed, and a drop in isomerization rate can be prevented.

<Step (A): Two-Step Reaction>

In the two-step reaction, no particular limitation is imposed on the reaction format, so long as the format ensure sufficient mixing of liquid phases through stirring. For example, any of batch, semi-batch, continuous, and other suitable reaction formats may be employed. Of these, semi-batch and continuous formats are preferably employed from the viewpoint of yield. In one specific embodiment of a semi-batch format, a liquid mixture of cyclohexene and m-xylene is fed to a reactor, $BF_3$ is subsequently fed thereto, and the reaction mixture is poured to ice-water, whereby 1-cyclohexyl-3,5-dimethylbenzene is recovered. In another embodiment of a continuous format, HF, m-xylene, and cyclohexene are fed to a first reaction tank, the reaction mixture is transferred from the first reaction tank with $BF_3$ to a second reaction tank. The resultant mixture is transferred from the bottom of the second reaction tank to ice or is decomposed by heat. Through continuously performing these operations, 1-cyclohexyl-3,5-dimethylbenzene can be produced.

In the two-step reaction, the ratio by mole of cyclohexene to m-xylene employed in alkylation of step (A), represented by cyclohexene/m-xylene, is 0.5 to 2.0 (mole), preferably 1.0 to 1.3 (mole). Such a limitation in range of amount of cyclohexene is also preferred from the viewpoint of production efficiency, since polycyclohexyl-m-xylene can be efficiently produced In the two-step reaction, HF employed in alkylation of step (A) is preferably a virtually anhydrous species. The ratio by mole HF to m-xylene, represented by HF/m-xylene, is 2 to 10 (mole), preferably 3 to 8 (mole). Such a limitation in range of amount of HF is advantageous from the viewpoint of production efficiency, since alkylation can be proceeded efficiently, and a large-scale reactor and a large-scale HF recovery unit are not needed.

The amount of HF (with respect to m-xylene) employed in subsequent isomerization/transalkylation is preferably the same as employed in alkylation of m-xylene, from the viewpoint of the production process. However, the amount may be increased without any problem in order to accelerate isomerization/transalkylation, and the range of the amount is the same as described in relation to alkylation. The ratio by mole of $BF_3$ to m-xylene employed in alkylation, represented by $BF_3$/m-xylene, is 1.1 to 3.0 (mole), preferably 1.5 to 2.0 (mole). Such a limitation in range of amount of $BF_3$ is preferred, since a favorable isomerization/trasnalkylation rate is maintained, and high production efficiency can be attained.

In the two-step reaction, alkylation of step (A) is preferably performed at −20° C. to 40° C., more preferably −10° C. to 20° C., which is recommended from the viewpoint of attaining the maximum reactivity. Such a limitation in range of reaction temperature is preferred, since side reactions such as decomposition or polymerization of cyclohexene and isomerization to a methylcyclopentyl compound are considerably suppressed, and a drop in alkylation rate can be prevented.

The subsequent isomerization/transalkylation is preferably performed at −20° C. to 20° C., more preferably −10° C. to 10° C., which is recommended from the viewpoint of attaining the maximum reactivity. Such a limitation in range of reaction temperature is preferred, since side reactions such as rearrangement of a methyl group and isomerization from a cyclohexyl group to a methylcyclopentyl compound are considerably suppressed, and a drop in isomerization/transalkylation rate can be prevented.

<Step (A): Recovery and Reuse of Catalysts>

In the present invention, HF and $BF_3$, serving as catalysts, can be recovered by virtue of high volatility, and the recovered catalysts can be reused. Therefore, in the production process of the present invention, disposal of the used catalysts is not needed. That is, the process of the invention is highly advantageous in terms of cost and can reduce load to the environment.

Specifically, HF and $BF_3$, serving as catalysts, are recovered through the following procedure. The reaction product mixture of step (A), in the case of either the single-step reaction or the two-step reaction, assumes an HF solution of 1-cyclohexyl-3,5-dimethylbenzene.HF—$BF_3$ complex. Through heating of the HF solution, the bond between 1-cyclohexyl-3,5-dimethylbenzene and HF—$BF_3$ is cleaved. When vaporized, HF and $BF_3$ can be recovered, and the recovered species can be reused. The thermal decomposition of the complex must be performed as rapidly as possible, so as to avoid undesired modification, isomerization, etc. From this standpoint, the thermal decomposition is preferably performed at 120 to 160° C., more preferably 130 to 150° C. The pressure at which the decomposition is performed depends on the temperature and solvent employed in the reaction and cannot be determined unequivocally. However, when benzene is employed as a solvent, decomposition is performed at about 140° C. and about 0.4 MPa, whereas when heptane is used, decomposition is performed at about 140° C. and about 0.2 MPa. In order to rapidly proceed thermal decomposition of the complex, the thermal decomposition is preferably performed in a solvent which is unlikely to cause side reaction with 1-cyclohexyl-3,5-dimethylbenzene in the presence of HF—$BF_3$ under reflux conditions. Examples of such a solvent include saturated hydrocarbons such as heptane.

After removal of the catalysts, 1-cyclohexyl-3,5-dimethylbenzene which has been formed through reaction between m-xylene and cyclohexene is in a state of dissolution in the solvent. Since the solvent is not needed in a subsequent step and possibly contains a by-product which impairs the subsequent reaction, 1-cyclohexyl-3,5-dimethylbenzene is preferably isolated through distillation before performing the subsequent reaction. The solvent which has been recovered at the distillation may be reused in thermal decomposition of the complex.

When the reaction product mixture of step (A) (HF solution) is thermally decomposed, the HF solution may be fed to a catalyst recovery tower. Examples of the catalyst recovery tower include a bubble-cap tower, a perforated plate tower, a packed tower, and a combination thereof (e.g., a perforated plate tower and a packed tower). These towers may or may not have an overflow weir or a downcomer. Examples of the tray include a perforated tray, a bubble tray, a bubble-cap tray, and a superflash tray. Conventionally employed fillers such as columnar, cyrindrical, spherical, and cubic fillers as well as specially designed regular or irregular fillers serving as high-performance fillers such as a Raschig ring are preferably employed.

When the reaction product mixture of step (A) (HF solution) is fed to such a catalyst recovery tower, a solution of 1-cyclohexyl-3,5-dimethylbenzene in the solvent employed in the reaction is recovered through the tower bottom. HF and $BF_3$ are recovered through the tower top, followed by cooling. After cooling, HF (b.p.: 19.4° C., at normal pressure) is isolated as liquid, while $BF_3$ is isolated as gas. If necessary, HF and $BF_3$ recovered through the tower top are pressurized and fed to a reactor of step (A), where they are reused.

<Step (B)>

Subsequently, step (B), represented by the following reaction scheme (3):

[F3]

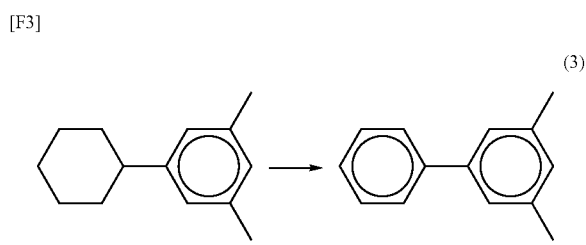

(3)

includes dehydrogenating 1-cyclohexyl-3,5-dimethylbenzene produced through step (A) in the presence of a dehydrogenation catalyst, to thereby yield 3,5-dimethylbiphenyl.

For dehydrogenating 1-cyclohexyl-3,5-dimethylbenzene, there may be employed a dehydrogenating catalyst formed of a noble metal (e.g., platinum, palladium, ruthenium, or iridium) supported on a customary carrier (e.g., activated carbon, alumina, or silica). In addition, a non-noble metal catalyst generally employed in dehydrogenation of cyclohexane such as sulfur, nickel, chromium oxide, or iron oxide may optionally be used. Among these catalysts, platinum is particularly preferred from the viewpoint of reaction activity. In consideration of catalyst cost, palladium is also preferred.

The temperature in step (B) is preferably 200 to 600° C., and the pressure is preferably 0.01 to 1.0 MPa. The time for dehydrogenation reaction is 1 to 24 hours. More preferably, the temperature is 225 to 350° C., and the pressure is 0.1 to 0.1 MPa, from the viewpoint of ease of removing hydrogen. Such a limitation in range of temperature is preferred, since side reactions are considerably suppressed, and a drop in dehydrogenation rate can be prevented.

The reaction format may be of a batch format in liquid phase or of a fixed bed flow format in gas phase. In the case of a batch format, the ratio by mass of catalyst to 1-cyclohexyl-3,5-dimethylbenzene is preferably 0.01 to 0.3, more preferably 0.03 to 0.1. Such a limitation in range of amount of catalyst is preferred from the viewpoint of production efficiency, since excessive retardation of dehydrogenation reaction is prevented. In the case where a flow manner on a fixed bed is employed, when the weight hourly space velocity (WHSV) is adjusted to 0.01 to 10 $hr^{-1}$, excellent reactivity and efficiency of the production can be attained, which is preferred. The reaction system may be diluted with a gas which is inert to dehydrogenation reaction such as nitrogen, argon, helium, or steam.

3,5-Dimethylbiphenyl produced through dehydrogenation of 1-cyclohexyl-3,5-dimethylbenzene does not affect the reaction represented by the reaction scheme (4). Thus, the 3,5-dimethylbiphenyl as is may be employed without purifying through distillation. However, preferably, after removal of the dehydrogenation catalyst, it is purified through distillation before employment in a subsequent reaction.

<Step (C)>

Step C, represented by the following reaction scheme (4):

[F4]

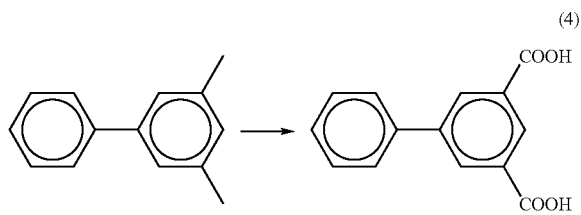

(4)

includes dissolving 3,5-dimethylbiphenyl produced in step (B) in a solvent, followed by oxidation in the presence of an oxidation catalyst, to thereby yield 5-phenylisophthalic acid.

The oxidation catalyst employed in step (C) contains a cobalt atom, a manganese atom, and a bromine atom. For example, a mixture of a compound containing a cobalt atom, a compound containing a manganese atom, and a compound containing a bromine atom is employed. Examples of the cobalt-atom-containing compound and the manganese-atom-containing compound include cobalt salts and manganese salts of an aliphatic carboxylic acid such as formic acid, acetic acid, propionic acid, oxalic acid, or maleic acid; those of an alicyclic carboxylic acid such a naphthenic acid; cobalt carbonates and manganese carbonates; and cobalt bromides and manganese bromides. Of these, acetates and bromides are preferred, with acetates being particularly preferred.

Examples of the bromine-atom-containing compound include inorganic bromides such as hydrogen bromide, sodium bromide, cobalt bromide, and manganese bromide; and organic bromides such as tetrabromoethane. Of these, hydrogen bromide, cobalt bromide, and manganese bromide are preferred, with hydrogen bromide being particularly preferred.

When cobalt bromide or manganese bromide is employed as the cobalt-atom-containing compound or the manganese-atom-containing compound, no additional bromine-atom-containing compound is required.

The solvent employed in step (C) is preferably a C1 to C5 aliphatic monocarboxylic acid. Examples of the carboxylic acid include formic acid, acetic acid, propionic acid, butyric acid, and mixtures thereof. Of these, acetic acid and propionic acid are preferred, with acetic acid being particularly preferred. In a preferred embodiment of step (C), the solvent is an aliphatic monocarboxylic acid solvent, the oxidation catalyst is a catalyst containing a cobalt atom, a manganese atom, and a bromine atom, and oxidation is performed by use of an oxygen-containing gas. In a more preferred embodiment, the solvent is acetic acid, the oxidation catalyst is a catalyst formed from cobalt acetate, manganese acetate, and hydrogen bromide.

The solvent preferably has a water content of 0.5 to 50 mass %, more preferably 3 to 15 mass %, particularly preferably 5 to 12 mass %. Such a limitation in range of water content is preferred, in order to prevent ensure prevention of reduction in oxidation activity, prolongation of reaction time, coloring of the formed product, and increase in the amount of solvent to be combusted.

The ratio by mass of 3,5-dimethylbiphenyl to solvent, represented by 3,5-dimethylbiphenyl/solvent, is preferably 0.2 to 10, more preferably 0.3 to 4, still more preferably 0.5 to 1.5. Such a limitation in range of ratio by mass of 3,5-dimethylbiphenyl is preferred, since clogging in a reactor through deposition of the formed product, deposition of crystals, and difficulty in purification through crystallization are avoided.

The oxidation catalyst concentration with respect to the solvent is preferably 200 to 10,000 ppm as metal atoms, more preferably 300 to 3,000 ppm, still more preferably 400 to 1,500 ppm. The atomic ratio of manganese to cobalt is preferably 0.1 to 10, more preferably 0.8 to 4. The atomic ratio of bromine to cobalt and manganese is 0.2 to 3, more preferably 0.5 to 1.5. When each metal concentration falls within the corresponding rage, 5-phenylisophthalic acid of good hue is yielded, and the amount of solvent to be combusted can be reduced to a very low level.

The reaction temperature employed in step (C) is preferably 140 to 230° C., more preferably 180 to 210° C. No particular limitation is imposed on the pressure, so long as the solvent maintains the liquid state. Generally, the reaction is performed at 1 to 2.5 MPa.

The oxygen-containing gas is preferably air. Preferably, the oxygen-containing gas is fed to the reaction mixture such that the oxygen concentration of the discharge gas during oxidation is maintained at 0.1 to 8%, more preferably 2 to 6%.

Through cooling the reaction mixture obtained in step (C) to 100° C. to room temperature, crude crystals of 5-phenylisophthalic acid can be deposited. Subsequently, the crystals are separated through filtration and washed with the same solvent as employed in the oxidation reaction, whereby crystals (purity: ≧99.9%) of 5-phenylisophthalic acid can be yielded.

No particular limitation is imposed on the oxidation reactor, and a stirring tank, a bubbling tank, etc. may be employed. Among these, a stirring tank is preferred, since the content in the reactor can be sufficiently stirred. No particular limitation is imposed on the reaction format, and any of batch, semi-batch, continuous may be employed. Of these, a continuous format, which is highly efficient, is preferably employed for performing the reaction on an industrial scale.

When a semi-batch format is employed, a titanium-made autoclave equipped with a gas-exhaust pipe having a reflux condenser, a gas-introducing pipe, and a stirrer is employed as a reactor. Firstly, a catalyst and a solvent are fed to the reactor, and the temperature inside the reactor is controlled to a predetermined level. Subsequently, the inside of the reactor is pressurized with air to a predetermined level, and a solvent and a source liquid for 3,5-dimethylbiphenyl are fed to the reactor. During feeding the source liquid, air (gas) is fed to the reactor in such a rate that the oxygen concentration of the exhaust gas is maintained at 0.1 to 8%. After completion of feeding the source liquid, the resultant mixture is maintained until the oxygen concentration of the exhaust gas exceeds 20%. The reaction mixture is cooled to room temperature, and the formed slurry is separated through filtration, whereby 5-phenylisophthalic acid can be yielded.

When a continuous format is employed, a catalyst and a solvent which would be placed firstly in a reactor in a semi-batch format, and a source liquid are fed together to a reactor. The reaction mixture liquid is removed through from the bottom of the reaction tank. The thus-removed reaction mixture is cooled, to thereby form a slurry containing 5-phenylisophthalic acid. The 5-phenylisophthalic acid of the present invention can be yielded through continuously performing the series of operations.

EXAMPLES

The present invention will next be described in more detail by way of Examples and Comparative Examples, which should not be construed as limiting the invention thereto.

Example 1

<Step (A): Single-Step Reaction>

To a temperature-controllable autoclave (made of SUS 316L, capacity: 500 mL) equipped with an electromagnetic stirrer, anhydrous HF 63.9 g (3.2 mol) and $BF_3$ 91.9 g (1.3 mol) were fed. The mixture in the autoclave was stirred, and the temperature thereof was maintained at −10° C. Subsequently, a source liquid (120.3 g) containing m-xylene and cyclohexene at a mole ratio of 1:1 (m-xylene 0.64 mol and cyclohexene 0.64 mol) was fed to the reactor at 3.0 g/min. After feeding of the source liquid, the resultant mixture was maintained for 20 min. Thereafter, the content of the reactor was poured in ice-water, followed by dilution with toluene and neutralization, to thereby form an oil layer. Through evaluation of the reaction, the percent conversion of m-xylene was found to be 92%, and the yield of 1-cyclohexyl-3,5-dimethylbenzene was found to be 77%.

<Step (A): Two-Step Reaction and Recovery of Catalysts>

To a temperature-controllable autoclave (made of SUS 316L, capacity: 10 L) equipped with an electromagnetic stirrer, anhydrous HF 1.0 kg (50 mol) was fed. The mixture in the autoclave was stirred, and the temperature thereof was maintained at 10° C. Subsequently, a source liquid (1.88 kg) containing m-xylene and cyclohexene at a mole ratio of 1:1 (m-xylene 10 mol and cyclohexene 10 mol) was fed to the reactor at 31.4 g/min. The temperature of the liquid was lowered to −10° C., and $BF_3$ (1.36 kg) was fed to the reactor at 11.6 g/min. After feeding of $BF_3$, the resultant mixture was maintained for 20 min.

Subsequently, the thus-formed HF solution of 1-cyclohexyl-3,5-dimethylbenzene.HF—$BF_3$ complex was fed to a catalyst recovery tower (inner diameter: 760 mm, length: 1,760 mm, filled with ½-inch Raschig rings made of Teflon) under heptane reflux conditions at a pressure of 0.4 MPa and a tower bottom temperature of 140° C. HF and $BF_3$ were recovered through the tower top, and a heptane solution containing 1-cyclohexyl-3,5-dimethylbenzene was separated through the bottom of the tower. The thus-obtained heptane solution was neutralized, to thereby form an oil layer. Through evaluation of the reactions, the percent conversion of m-xylene was found to be 97%, and the yield of 1-cyclohexyl-3,5-dimethylbenzene was found to be 92%. The obtained oil layer was distilled by means of a rectification tower having a theoretical stages of 20, whereby 1.1 kg of 1-cyclohexyl-3,5-dimethylbenzene (purity: 99%) was yielded.

<Step (B)>

To a 3 L three-neck flask equipped with a magnetic stirrer, a distillation head, and a condenser, a platinum-on-carbon catalyst (platinum content: 2 mass %) (64.5 g (in wet state), and water content: 53.5%) and 1-propanol (300 mL) were added under nitrogen. Subsequently, the three-neck flask was heated until a water/propanol azeotropic mixture was completely evaporated. After complete removal of water in the system, the reaction mixture was cooled to room temperature, and 1-cyclohexyl-3,5-dimethylbenzene (713 g, 4.45 mol) produced in the two-step reaction of the aforementioned step (A) was added to the cooled mixture. Subsequently, the distillation head and the condenser were removed from the flask, and a Dimroth condenser was attached to the flask, followed by heating the system in the flask. Boiling of the reaction mixture started at 250° C., and the temperature gradually elevated and eventually reached 280° C. Six hours after the start of boiling, heating was stopped, and the heated mixture was cooled to room temperature. The employed catalyst was removed through filtration from the reaction mixture, to thereby obtain an oil layer. Through evaluation of the reactions, the percent conversion of 1-cyclohexyl-3,5-dimethylbenzene was found to be 99.8%, and the yield of 3,5-dimethylbiphenyl was found to be 98.4%. The obtained oil layer was distilled by means of a rectification tower having a theoretical stages of 20, whereby 580 g of 3,5-dimethylbiphenyl (purity: 99.8%) was yielded.

<Step (C)>

A titanium-made autoclave (capacity: 2 L) equipped with a gas-exhaust pipe having a reflux condenser, a gas-introducing pipe, and a stirrer was employed as a reactor. To the reactor, cobalt acetate tetrahydrate (0.76 g) serving as a catalyst, manganese acetate tetrahydrate (0.75 g), aqueous hydrogen bromide solution (concentration: 48 mass %) (0.74 g), and acetic acid (water content: 5 mass %) (118.2 g) as a solvent were added. Under air, the system was pressurized to 1.8 MPa, and the temperature of the liquid was elevated to 200° C. Thereafter, a source solution obtained by mixing with acetic acid (179.5 g) and 3,5-dimethylbiphenyl (170.9 g) was fed in an amount of 264 g to the reactor at 4.8 g/min. The flow rate of exhaust gas during feeding of the source solution was controlled such that the oxygen concentration of the exhaust gas was maintained at 3 to 4%. Specifically, the flow rate was about 260 to about 270 L/H. After feeding of the source solution, the resultant mixture was maintained (for about 9 min) until the oxygen concentration of the exhaust gas exceeded 20%. The reactor was cooled to room temperature, and the formed slurry was separated through filtration. The slurry was washed with acetic acid and drying, to thereby yield 140 g crystals of 5-phenylisophthalic acid (purity: 99.9%). The yield of 5-phenylisophthalic acid was 86%.

Example 2

<Step (A): Reuse of Catalysts>

The procedure of the two-step reaction of step (A) was repeated, except that the recovered HF ($BF_3$ content: 5 mass %) and $BF_3$. More specifically, the recovered HF ($BF_3$ content: 5 mass %) was used instead of anhydrous HF, and the recovered $BF_3$ was used instead of $BF_3$. Through evaluation of the reactions, the percent conversion of m-xylene was found to be 95%, and the yield of 1-cyclohexyl-3,5-dimethylbenzene was found to be 90%.

Industrial Applicability

According to the process of the present invention, 5-phenylisophthalic acid can be produced at high selectivity and yield. The industrially advantageous process realizes recovery and reuse of a catalyst. The 5-phenylisophthalic acid produced through the production process of the present invention is a useful starting material for producing dyes, perfumes, pharmaceuticals, pesticides, electronic functional materials, and optical functional materials.

The invention claimed is:

1. A process for producing 5-phenylisophthalic acid represented by formula (1):

[F1]

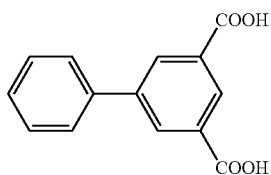

(1)

characterized in that the process comprises the following steps (A) to (C):
   (A) reacting m-xylene with cyclohexene in the presence of hydrogen fluoride and boron trifluoride, to thereby produce 1-cyclohexyl-3,5-dimethylbenzene;
   (B) dehydrogenating the 1-cyclohexyl-3,5-dimethylbenzene produced in step (A) in the presence of a dehydrogenation catalyst, to thereby produce 3,5-dimethylbiphenyl; and
   (C) dissolving the 3,5-dimethylbiphenyl produced in step (B) in a solvent and oxidizing the 3,5-dimethylbiphenyl in the co-presence of an oxidation catalyst, to thereby produce 5-phenylisophthalic acid wherein, in step (A), m-xylene is alkylated with cyclohexene in the presence of hydrogen fluoride, and, subsequently, isomerization/transalkylation is performed in the presence of hydrogen fluoride and boron trifluoride;

wherein the dehydrogenation catalyst employed in step (B) is a catalyst containing platinum and/or palladium, supported on a carrier; and wherein, in step (C), the solvent is acetic acid containing 3 to 15 mass % of water, the oxidation catalyst is a catalyst containing a cobalt atom, a manganese atom, and a bromine atom, and oxidation is performed by an oxygen-containing gas.

2. A process for producing 5-phenylisophthalic acid as described in claim 1, wherein the oxidation catalyst contains cobalt acetate, manganese acetate, and hydrogen bromide.

3. A process for producing 5-phenylisophthalic acid as described in claim 1, wherein, in step (A), hydrogen fluoride and boron trifluoride are recovered and reused.

4. A process for producing 5-phenylisophthalic acid as described in claim 1, wherein the amount of water in the solvent in step (C) is 5 to 12 mass %.

5. A process for producing 5-phenylisophthalic acid as described in claim 1, wherein, in step (C), a ratio by mass of 3,5-dimethylbiphenyl to the solvent is 0.2 to 10.

6. A process for producing 5-phenylisophthalic acid as described in claim 1, wherein, in step (C), a ratio by mass of 3,5-dimethylbiphenyl to the solvent is 0.5 to 1.5.

7. A process for producing 5-phenylisophthalic acid as described in claim 2, wherein, in step (A), hydrogen fluoride and boron trifluoride are recovered and reused.

* * * * *